United States Patent
Ci

(10) Patent No.: US 10,383,824 B2
(45) Date of Patent: Aug. 20, 2019

(54) SOLID BEVERAGE FOR CONDITIONING YIN DEFICIENCY CONSTITUTION AND METHOD FOR PRODUCING THE SAME

(71) Applicant: Zhonghua Ci, Beijing (CN)

(72) Inventor: Zhonghua Ci, Beijing (CN)

(*) Notice: Subject to any disclaimer, the term of this patent is extended or adjusted under 35 U.S.C. 154(b) by 0 days.

(21) Appl. No.: 15/878,377

(22) Filed: Jan. 23, 2018

(65) Prior Publication Data

US 2019/0160011 A1     May 30, 2019

(30) Foreign Application Priority Data

Nov. 30, 2017  (CN) .......................... 2017 1 1240639

(51) Int. Cl.

| | |
|---|---|
| *A61K 36/605* | (2006.01) |
| *A61K 9/16* | (2006.01) |
| *A61K 36/8967* | (2006.01) |
| *A61K 35/618* | (2015.01) |
| *A61K 36/9064* | (2006.01) |
| *A61K 36/88* | (2006.01) |
| *A61K 36/899* | (2006.01) |
| *A61K 9/00* | (2006.01) |
| *A23L 2/02* | (2006.01) |
| *A23L 17/50* | (2016.01) |
| *A23L 2/60* | (2006.01) |
| *A23L 29/212* | (2016.01) |
| *A61K 36/736* | (2006.01) |

(52) U.S. Cl.
CPC .............. *A61K 9/1682* (2013.01); *A23L 2/02* (2013.01); *A23L 2/60* (2013.01); *A23L 17/50* (2016.08); *A23L 29/212* (2016.08); *A61K 9/0095* (2013.01); *A61K 9/1617* (2013.01); *A61K 9/1652* (2013.01); *A61K 35/618* (2013.01); *A61K 36/605* (2013.01); *A61K 36/736* (2013.01); *A61K 36/88* (2013.01); *A61K 36/899* (2013.01); *A61K 36/8967* (2013.01); *A61K 36/9064* (2013.01); *A23V 2002/00* (2013.01)

(58) Field of Classification Search
None
See application file for complete search history.

(56) References Cited

FOREIGN PATENT DOCUMENTS

CN         102166310 A  *  8/2011

* cited by examiner

*Primary Examiner* — Susan Hoffman
(74) *Attorney, Agent, or Firm* — Novick, Kim & Lee, PLLC; Allen Xue

(57) ABSTRACT

Provided is a solid beverage for conditioning yin deficiency constitution. The solid beverage includes the following components in parts by weight: 30-55 parts of smoked plum, 29-51 parts of lilium brownii, 27-50 parts of polygonatum odoratum, 30-52 parts of mulberry leaves, 27-48 parts of mulberries, 26-58 parts of fresh reed rhizome, 67-94 parts of oysters, 3-15 parts of amomum villosum, 27-50 parts of dextrin, 16-43 parts of maltodextrin, 38-70 parts of soluble starch and 0.15-0.35 parts of aspartame. The solid beverage is simple and convenient to prepare, the raw materials used are all medicinal materials with dual-purpose of drug and food, and the auxiliary materials used also meet the national standard GB2760-2011 (the National Food Safety Standard for Food Additive Use). Thus, the solid beverage is safe to consume and good in taste, a long-term consumption of the solid beverage has certain effects on the improvement of yin deficiency constitution, and the production process thereof is suitable for industrial mass production.

10 Claims, 2 Drawing Sheets

SOLID BEVERAGE FOR CONDITIONING YIN DEFICIENCY CONSTITUTION AND METHOD FOR PRODUCING THE SAME

CROSS-REFERENCE TO RELATED APPLICATIONS

This application claims priority under 35 U.S.C. § 119 to a Chinese Patent Application No. 201711240639.7 filed Nov. 30, 2017, in the State Intellectual Property Office of China, the entire contents of which are hereby incorporated by reference.

TECHNICAL FIELD

The present invention relates to the field of health foods, and particularly to a solid beverage for conditioning yin deficiency constitution and a method for producing the same.

BACKGROUND

In Classification and Determination of Constitution in Traditional Chinese Medicine, the China Association of Chinese Medicine classifies body constitutions of the human body into nine types, i.e., yin-yang harmony constitution, yang deficiency constitution, yin deficiency constitution, qi deficiency constitution, phlegm-dampness constitution, damp-heat constitution, qi stagnation constitution, blood stasis constitution and allergic constitution, most of which are sub-healthy states.

The yin deficiency constitution means that, when internal organs are dysfunctional, the syndromes of yin-fluid deficiency in the body and production of endogenous heat due to yin deficiency will easily occur, which are usually represented by emaciation of the body, tidal reddening of the cheeks, feverishness in palms and soles, tidal fever and night sweating, upset irritability, xerostomia, hair and skin dryness, and dry and red tongue with little or even no coating, and are mainly caused by invasion of pathogenic dryness-heat, overeating of febrile and dry food, excessive griefs and sorrow, intemperance in sexual life and long illness. The tendency of morbidity is: being susceptible to consumptive disease, seminal emission, insomnia, etc., being resistant to winter but nonresistant to summer, and being nonresistant to summer-heat, heat and pathogenic dryness.

Such sub-healthy constitution as yin deficiency constitution belongs to chronic diseases and has a relatively long disease course, and requires a long-term medication and gradual conditioning, in order to achieve the effects of tonifying qi and nourishing qi. The dosage forms commonly used in the traditional Chinese medicine are decoctions and Chinese patent medicine such as pills and the like. Decoctions usually have relatively good efficacy, but the administration thereof is complicated, and the taste thereof is poor, if the decoctions need to be administered for a long time, it is difficult for a patient to keep taking the decoctions. Moreover, the efficacy of the pills is relatively poor.

Food is the best product for human beings to prevent diseases and keep healthy. The theory that "medicine and food share a common origin" is one of the most valuable contributions made by the original Chinese medicine to human beings. It is described in the Rites of Zhou•Offices of the Heaven•Medicine that "diseases are treated with the five flavors, the five grains and the five medicines", which demonstrates the physical health-care functions of food. The method of regulating body functions using the characteristics of food so as to obtain health or prevent or treat diseases is called dietary therapy. However, "therapy" is inferior to "nourishing", and food nourishing is an approach to increase resistance against diseases and enhance immunity by eating tonic food according to food nutritions in combination with the body conditions, so as to strengthen the body and prolong the life. It is described in Prescriptions Worth a Thousand Gold that "a physician should first know the cause of a disease to know why the disease is developed and treat the disease with food materials. Only when food materials are unable to treat the disease, can drugs be used." Thus, dietary therapy was not only the basic therapeutic approach of the physicians at that time, but also an important criterion for determining whether a physician was a great physician.

It is mentioned in the Inner Canon of the Yellow Emperor that "the superior physician prevents illness, the mediocre physician attends to impending illness, and the inferior physician treats actual illness", wherein the phrase "prevent illness" means taking corresponding measures to prevent the occurrence and development of diseases. The body constitution determines the health of people and determines the susceptibility to diseases. Faced with the situations that there are various diseases in modern society, the age of onset becomes lower and lower and there are more and more sub-healthy people, dietary therapy gets more and more popular with the consumers due to its advantages of being healthy and natural, and with respect to the diseases that are easy to develop, it is of great significance to develop a food product that has the functions of life nourishing and health protection, has a good taste and conditions the yin deficiency constitution, by using modern scientific technologies and methods and the theory that "medicine and food share a common origin", referring to the precious Chinese traditional life nourishing experience in combination with good accumulation of the traditional Chinese medicine on the aspect of conditioning yin deficiency constitution.

DISCLOSURE OF THE INVENTION

The main object of the present invention is to provide a life nourishing and health protecting food product for conditioning yin deficiency constitution.

In order to achieve the above object, according to one aspect of the present invention, there is provided a solid beverage for conditioning yin deficiency constitution.

The solid beverage for conditioning yin deficiency constitution according to the present invention comprises the following components in parts by weight: 30-55 parts of smoked plum, 29-51 parts of lilium brownii, 27-50 parts of polygonatum odoratum, 30-52 parts of mulberry leaves, 27-48 parts of mulberries, 26-58 parts of fresh reed rhizome, 67-94 parts of oysters, 3-15 parts of amomum villosum, 27-50 parts of dextrin, 16-43 parts of maltodextrin, 38-70 parts of soluble starch and 0.15-0.35 parts of aspartame.

Further, the solid beverage for conditioning yin deficiency constitution of the present invention comprises the following components in parts by weight: 34-47 parts of smoked plum, 35-45 parts of lilium brownii, 33-47 parts of polygonatum odoratum, 36-48 parts of mulberry leaves, 30-43 parts of mulberries, 31-50 parts of fresh reed rhizome, 75-87 parts of oysters, 5-11 parts of amomum villosum, 33-44 parts of dextrin, 20-35 parts of maltodextrin, 48-60 parts of soluble starch and 0.2-0.3 parts of aspartame.

Further, the solid beverage for conditioning yin deficiency constitution of the present invention comprises the following components in parts by weight: 40 parts of smoked plum, 40 parts of lilium brownii, 40 parts of polygonatum odoratum, 40 parts of mulberry leaves, 40 parts of mulberries, 40 parts of fresh reed rhizome, 80 parts of oysters, 8 parts of amomum villosum, 37 parts of dextrin, 31 parts of maltodextrin, 56 parts of soluble starch and 0.25 parts of aspartame.

In order to achieve the above object, according to another aspect of the present invention, there is provided a method for producing a solid beverage for conditioning yin deficiency constitution.

The method for producing a solid beverage for conditioning yin deficiency constitution according to the present invention comprises the steps of:

(1) preparation of raw materials: subjecting smoked plum, lilium brownii, polygonatum odoratum, mulberry leaves, mulberry fruits, oysters, fresh reed rhizome and amomum villosum to impurity removal, cleansing, cutting and pulverization, and then mixing them for later use;

(2) decoction: decocting the mixture resulting from step (1) with water twice to obtain a traditional Chinese medicine liquid;

(3) concentration: pumping the traditional Chinese medicine liquid prepared in step (2) into an inspissator through a pipe to concentrate the same into thick paste; and (4) wet granulation: mixing and stirring dextrin, maltodextrin, soluble starch and aspartame to obtain a mixture adjuvant, adding the thick paste prepared in step (3) to the mixture adjuvant, and stirring the same for granulation.

Further, the two-time decoction process in step (2) is carried out as follows:

the first decoction: adding water that is 10 times the weight of the mixture prepared in step (1), heating and boiling the resultant mixture, and pumping the liquid medicine into a stainless-steel liquid medicine storage tank through a pipeline filter immediately after boiling for 1.5 hours (starting from boiling); and the second decoction: adding water that is 8 times the weight of the mixture prepared in step (1), heating and boiling the resultant mixture, and pumping the liquid medicine into the stainless-steel liquid medicine storage tank through the pipeline filter immediately after boiling for 1.5 hours (starting from boiling) to evenly mix the liquid medicine with the liquid medicine obtained from the first decoction.

Further, the temperature for the concentration in step (3) is 70-80° C., and the relative density of the prepared thick paste is 1.2-1.5 at the temperature of 50° C.

Further, the wet granulation in step (4) comprises the steps of:

(4.1) dry mixing: putting dextrin, maltodextrin, soluble starch and aspartame into an efficient mixer-granulator for mixing and stirring for 15 minutes to obtain a mixture adjuvant;

(4.2) primary sieving: adding batchwise the thick paste extracted from step (3) to the mixture adjuvant for mixing, stirring and granulation at the cutting speed I and the stirring speed I to obtain a soft material which is then subjected to primary sieving;

(4.3) drying: putting the sieved particles prepared from step (4.2) into a boiling dryer for drying; and (4.4) secondary sieving: carrying out secondary sieving by using a wig-wag machine.

Further, the sieve for the primary sieving is a 12-mesh sieve, and the sieve for the secondary sieving is a 10-mesh sieve.

Further, in the drying process in step (4.3), the temperature of the materials is controlled to be 70-80° C., and the moisture of the final materials is controlled to be 5% or less.

Further, after the secondary sieving, the method further comprises a particle selecting step to select particles of 10-60 meshes.

The solid beverage of the present invention is simple and convenient to prepare, the raw materials used are all medicinal materials with dual-purpose of drug and food, and the auxiliary materials used also meet the national standard GB2760-2011 (the National Food Safety Standard for Food Additive Use). Thus, the solid beverage is safe to consume and good in taste, and has certain effects on the improvement of yin deficiency constitution, and the production process thereof is suitable for industrial mass production.

BRIEF DESCRIPTION OF DRAWINGS

The accompanying drawings, which constitute a part of the present application, are used to provide a further understanding of the present invention, so that other features, objects and advantages of the present application become more obvious. The illustrative drawings for embodiments of the present invention and the description thereof are used to explain the present invention, rather than constitute an improper limitation on the present invention. In the drawings.

DETAILED DESCRIPTION OF EMBODIMENTS

Figure 1:
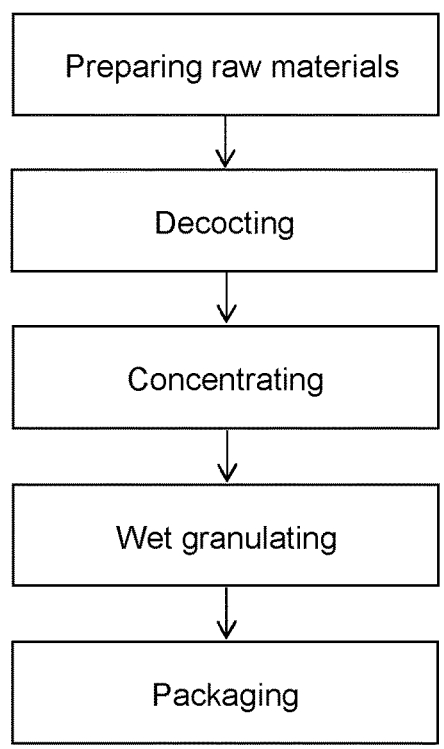
FIG. 1 is a production process of a solid beverage according to an embodiment of the present invention.

In order to enable a person skilled in the art to better understand the solutions of the present application, the technical solutions of the embodiments of the present invention will be described clearly and completely below with reference to the drawings of the embodiments of the present application. Apparently, the embodiments described are some of the embodiments of the present application, rather than all of the embodiments. All the other embodiments that are obtained by a person skilled in the art without inventive effort on the basis of the embodiments of the present application shall be covered by the protection scope of the present application.

In addition, the term "comprise" and any variant thereof are intended to cover non-exclusive inclusion, for example, a product comprising a series of raw materials or a method comprising a series of steps is not necessarily limited to the raw materials or the steps listed clearly, but can include other steps or raw materials that are not clearly listed or are inherent to the method and product.

It should be noted that the embodiments of the present application and the features of the embodiments can be combined with each other if there is no conflict. The present application will be described in detail below with reference to the accompanying drawings and embodiments.

The main object of the present invention is to provide a life nourishing and health protecting food product for conditioning yin deficiency constitution.

In order to achieve the above object, according to one aspect of the present invention, there is provided a solid beverage for conditioning yin deficiency constitution.

The solid beverage for conditioning yin deficiency constitution according to the present invention comprises the following components in parts by weight: 30-55 parts of smoked plum, 29-51 parts of lilium brownii, 27-50 parts of polygonatum odoratum, 30-52 parts of mulberry leaves, 27-48 parts of mulberries, 26-58 parts of fresh reed rhizome, 67-94 parts of oysters, 3-15 parts of amomum villosum, 27-50 parts of dextrin, 16-43 parts of maltodextrin, 38-70 parts of soluble starch and 0.15-0.35 parts of aspartame.

Smoked plum is sour and astringent in flavor and neutral in nature; acts on liver, spleen, lung and large intestine; has the efficacies of astringing the lung, astringing the intestines, promoting the secretion of saliva or body fluid, and calming ascaris; and is used for chronic cough caused by lung deficiency, prolonged diarrhea and dysentery, deficiency-heat consumptive thirst, ascaris-caused syncope, vomiting and abdominal pain.

Lilium brownii is sweet in flavor and cold in nature; acts on heart and lung; has the efficacies of nourishing yin, moistening the lung, clearing away the heart fire and tranquillizing; and is used for yin deficiency and irritating dry cough, over-strained cough, hemoptysis, dysphoria, pavor, insomnia and dreamful sleep, and trance.

Polygonatum odoratum is sweet in flavor and neutral in nature; acts on lung and stomach; has the efficacies of nourishing yin, moistening the lung, promoting the secretion of saliva or body fluid, and nourishing the stomach; and is used for yin deficiency and irritating dry cough, polydipsia and mouth dryness, and internal-heat consumptive thirst.

Mulberry leaves are bittersweet in flavor and cold in nature; act on lung and liver; have the efficacies of dispelling wind and heat from the body, clearing away the lung-heat and moistening dryness, calming the liver and improving acuity of vision, and cooling blood for hemostasis; and are used for wind-heat type common cold, onset of epidemic febrile disease, cough due to the lung heat, vertigo due to liver-yang hyperactivity, bloodshot eyes and being dimsighted, hemoptysis and hematemesis due to frenetic blood heat.

Mulberries are cold in nature and sweet and sour in flavor; act on heart, liver and kidney; have the efficacies of enriching blood and nourishing yin, promoting the secretion of saliva or body fluid and moistening dryness; and are used for vertigo and tinnitus, palpitation and insomnia, premature graying of hair, constipation, thirst due to fluid deficiency, internal-heat consumptive thirst, blood deficiency constipation, tonifying liver, tonifying kidney, extinguishing wind, nourishing liquid and the treatment of yin deficiency of liver and kidney.

Reed rhizome is sweet in flavor and cold in nature; acts on lung and stomach; has the efficacies of clearing away heat and purging pathogenic fire, helping produce saliva and slaking thirst, relieving restlessness, arresting vomiting and diuresis; and is used for pyreticosis polydipsia, cough due to the lung heat, internal-heat consumptive thirst, sore, ulcer and pyogenic infections.

Oysters are salty in flavor and slightly cold in nature; acts on liver and kidney; have the efficacies of restraining the hyperactivity of the liver yang, softening hardness to dissipate stagnation, astringency, inducing astringency; and are used for dizziness, liver wind convulsion, scrofula, subcutaneous nodes, spontaneous perspiration, night sweating, spermatorrhea, metrorrhagia and metrostaxis, and morbid leukorrhea.

Amomum villosum is acrid in flavor and damp in nature; acts on spleen, stomach and kidney; has the efficacies of resolving dampness and promoting appetite, warming spleen and stopping diarrhea, regulating vital energy and preventing miscarriage; and is used for dampness turbidity blocking, fullness and distending pain in the chest and upper abdomen and anorexia, deficiency-cold of the spleen and stomach, vomiting and diarrhea, hyperemesis gravidarum, and fetal irritability.

People with yin deficiency constitution often have the syndromes of yin-fluid deficiency and production of endogenous heat due to yin deficiency, which are usually represented by emaciation of the body, mouth dryness and throat dryness, tidal reddening of the cheeks, feveringness in palms and soles, tidal fever and night sweating, upset irritability, xerostomia, and dry and red tongue with little or even no coating. Yin deficiency in the five internal organs is clinically common, and besides the aforesaid clinical manifestations, corresponding lesions of each organ can be seen and therefore different symptoms are presented. The conditioning of the yin deficiency constitution takes the principle of nourishing yin and conditioning the body. This prescription mainly includes yin-nourishing drugs, and as the yin deficiency constitution mainly results from long-term consumption of yin fluid in the body, most of the common yin-nourishing and tonifying materials are greasy and affect the transportation and transformation function of spleen and stomach, and in this prescription, drugs are selected based on the principle of being nourishing but not greasy, which are light and yin-nourishing materials and aim to prevent the occurrence of the case where long-term administration of common yin-nourishing drugs increases greasiness and hurts stomach, wherein smoked plum nourishes yin and promotes the secretion of saliva or body fluid; lilium brownii, polygonatum odoratum, fresh reed rhizome and mulberry leaves are light, moisturizing and yin-nourishing; mulberries do not nourish kidney yin; oysters restrain yang and tonify yin; amomum villosum prevents the generation of greasiness and hurt to stomach. These drugs are harmonized, nourish yin and promote the secretion of saliva or body fluid, and are tonifying but not greasy. In addition, dextrin, maltodextrin and aspartame, on the one hand, can give play to medicinal effect and balance the nutritional ingredients, and on the other hand, can be used for flavoring.

As shown in FIG. 1, the method for producing a solid beverage for conditioning yin deficiency constitution comprises the steps of:

(1) preparation of raw materials: subjecting smoked plum, lilium brownii, polygonatum odoratum, mulberry leaves, mulberry fruits, oysters, fresh reed rhizome and amomum villosum to impurity removal, cleansing, cutting and pulverization, and then mixing them for later use, wherein the proportion of each raw material provided in the present invention is used herein;

(2) decoction: decocting the mixture resulting from step (1) with water twice to obtain a traditional Chinese medicine liquid;

(3) concentration: pumping the traditional Chinese medicine liquid prepared in step (2) into an inspissator through a pipe to concentrate the same into thick paste;

(4) wet granulation: mixing and stirring dextrin, maltodextrin, soluble starch and aspartame to obtain a mixture adjuvant, adding the thick paste prepared in step (3) to the mixture adjuvant, and stirring the same for granulation; and (5) packaging: subjecting the product resulting from the wet granulation to the packaging step to obtain a finished product.

The purpose of step (1) is to remove fat from the seed medicinal materials, pulverize the resultant seed medicinal materials and pass them through a 2-mesh sieve; the rhizomatic medicinal materials contain cellulose, and are rich in starch, and cutting or pulverization extraction can effectively retain the target ingredients thereof, and prevent polysaccharide swelling; and cleansing can remove impurities and soil, and effectively reduce the residuals of pollutants such as heavy metals and pesticides.

The two-time decoction process in step (2) is carried out as follows: the first decoction: adding water that is 10 times the weight of the mixture prepared in step (1), heating and boiling the resultant mixture, and pumping the liquid medicine into a stainless-steel liquid medicine storage tank through a pipeline filter immediately after boiling for 1.5 hours (starting from boiling); and the second decoction: adding water that is 8 times the weight of the mixture prepared in step (1), heating and boiling the resultant mixture, and pumping the liquid medicine into the stainless-steel liquid medicine storage tank through the pipeline filter immediately after boiling for 1.5 hours (starting from boiling) to evenly mix the liquid medicine with the liquid medicine obtained from the first decoction.

The temperature for the concentration in step (3) is 70-80° C., and the relative density of the prepared thick paste is 1.2-1.5 at the temperature of 50° C. The low-temperature evaporation can effectively reduce the decomposition of thermosensitive components, such as citric acid, malic acid, oxalic acid and other organic acids, and leads to high concentration efficiency without discharge of solvent steam, which facilitates evaporation, and is pollution-free to the environment, as it is carried out in an airtight space.

Figure 2:
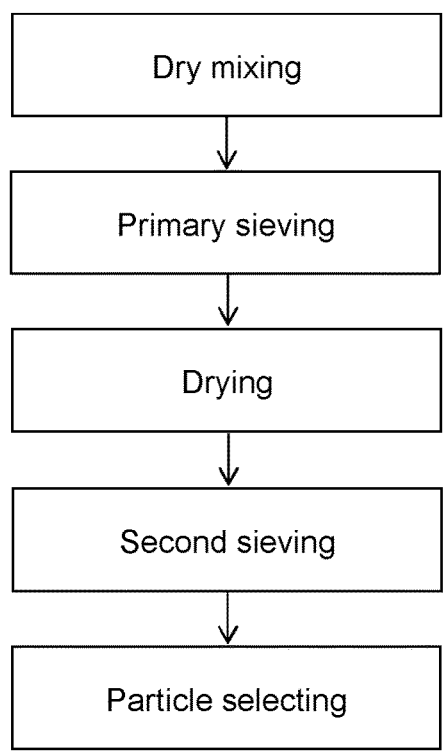
FIG. 2 is the specific steps of wet granulation in the production process of the solid beverage according to an embodiment of the present invention.

As shown in FIG. 2, the wet granulation in step (4) comprises the steps of:

(4.1) dry mixing: putting dextrin, maltodextrin, soluble starch and aspartame into an efficient mixer-granulator for mixing and stirring for 15 minutes to obtain a mixture adjuvant, wherein the proportion of each raw material provided in the present invention is used herein;

(4.2) primary sieving: adding batchwise the thick paste extracted from step (3) to the mixture adjuvant for mixing, stirring and granulation at the cutting speed I and the stirring speed I to obtain a soft material which is then subjected to primary sieving, wherein stirring granulation can preferably prevent separation of the components, and since segregation phenomenon can easily occur due to the existence of differences in the particle size and density of the mixed extract components, granulation not only can effectively solve this problem, but also can remarkably improve the solubility;

(4.3) drying: putting the sieved particles prepared from step (4.2) into a boiling dryer for drying, wherein fluidized drying can effectively control the particle size distribution and control the product moisture; and (4.4) secondary sieving: carrying out secondary sieving by using a wig-wag machine, wherein by means of the secondary sieving, it is possible to control the particle distribution, bulk density and compactness.

In the above steps, the sieve for the primary sieving is a 12-mesh sieve, and the sieve for the secondary sieving is a 10-mesh sieve.

In the drying process in the above step (4.3), the temperature of the materials is controlled to be 70-80° C., and the moisture of the final materials is controlled to be 5% or less. In this step, pot turning can be frequently carried out according to the drying condition of the materials, so that the final material moisture meets the requirements.

On the basis of the implementation modes above, after the secondary sieving, the method further comprises a particle selecting step to select particles of 10-60 meshes. By means of particle selection, it is possible to improve the appearance and uniformity of the product particles. In practice, after the completion of the particle selection, it is feasible to make a record and tag the product to indicate the product name, the lot number, the specification, the net weight, the production date, the post name and the responsible person, fill in the equipment receipt, and transfer the product into an intermediate station.

Embodiment 1

The solid beverage for conditioning yin deficiency constitution comprises the following components in parts by weight: 30 parts of smoked plum, 29 parts of lilium brownii, 27 parts of polygonatum odoratum, 30 parts of mulberry leaves, 27 parts of mulberries, 26 parts of fresh reed rhizome, 67 parts of oysters, 3 parts of amomum villosum, 27 parts of dextrin, 16 parts of maltodextrin, 38 parts of soluble starch and 0.15 parts of aspartame.

The production method thereof is as follows:

(1) preparation of raw materials: subjecting smoked plum, lilium brownii, polygonatum odoratum, mulberry leaves, mulberry fruits, oysters, fresh reed rhizome and amomum villosum to impurity removal, cleansing, cutting and pulverization, and then mixing them for later use;

(2) decoction: decocting the mixture resulting from step (1) with water twice to obtain a traditional Chinese medicine liquid, wherein the two-time decoction process is carried out as follows:

the first decoction: adding water that is 10 times the weight of the mixture prepared in step (1), heating and boiling the resultant mixture, and pumping the liquid medicine into a stainless-steel liquid medicine storage tank through a pipeline filter immediately after boiling for 1.5 hours (starting from boiling); and the second decoction: adding water that is 8 times the weight of the mixture prepared in step (1), heating and boiling the resultant mixture, and pumping the liquid medicine into the stainless-steel liquid medicine storage tank through the pipeline filter immediately after boiling for 1.5 hours (starting from boiling) to evenly mix the liquid medicine with the liquid medicine obtained from the first decoction;

(3) concentration: pumping the traditional Chinese medicine liquid prepared in step (2) into an inspissator through a pipe to concentrate the same into thick paste, wherein the temperature for the concentration is 70° C., and the relative density of the prepared thick paste is 1.2 at the temperature of 50° C.;

(4) wet granulation (4.1) dry mixing: putting dextrin, maltodextrin, soluble starch and aspartame into an efficient mixer-granulator for mixing and stirring for 15 minutes to obtain a mixture adjuvant;

(4.2) primary sieving: adding batchwise the thick paste extracted from step (3) to the mixture adjuvant for mixing, stirring and granulation at the cutting speed I and the stirring speed I to obtain a soft material which is then subjected to primary sieving using a 12-mesh sieve;

(4.3) drying: putting the sieved particles prepared from step (4.2) into a boiling dryer for drying, wherein the temperature of the materials is controlled to be 70° C., and the moisture of the final materials is controlled to be 5%;

(4.4) secondary sieving: carrying out secondary sieving by using a wig-wag machine, using a 10-mesh sieve; and (4.5) particle selecting: selecting the particles of 10-60 meshes; and (5) packaging: bagging the particles, which have been mixed and have been tested to be qualified, by an automatic packaging machine according to standard operation procedures, wherein the appearance and the loading amount of the bag are timely detected, and corresponding measures are taken if there occurs any abnormality, the bagged particles are sealed and stored in a clean container, with the product name, the lot number, the number, the date and the like indicated for later use; the reference loading amount is 8 g per bag, and the loading limit is 8 g/bag±5%.

Embodiment 2

The solid beverage for conditioning yin deficiency constitution comprises the following components in parts by weight: 55 parts of smoked plum, 51 parts of lilium brownii, 50 parts of polygonatum odoratum, 52 parts of mulberry leaves, 48 parts of mulberries, 58 parts of fresh reed rhizome, 94 parts of oysters, 15 parts of amomum villosum, 50 parts of dextrin, 43 parts of maltodextrin, 70 parts of soluble starch and 0.35 parts of aspartame.

The production method thereof is as follows:

(1) preparation of raw materials: subjecting smoked plum, lilium brownii, polygonatum odoratum, mulberry leaves, mulberry fruits, oysters, fresh reed rhizome and amomum villosum to impurity removal, cleansing, cutting and pulverization, and then mixing them for later use;

(2) decoction: decocting the mixture resulting from step (1) with water twice to obtain a traditional Chinese medicine liquid, wherein the two-time decoction process is carried out as follows:

the first decoction: adding water that is 10 times the weight of the mixture prepared in step (1), heating and boiling the resultant mixture, and pumping the liquid medicine into a stainless-steel liquid medicine storage tank through a pipeline filter immediately after boiling for 1.5 hours (starting from boiling); and the second decoction: adding water that is 8 times the weight of the mixture prepared in step (1), heating and boiling the resultant mixture, and pumping the liquid medicine into the stainless-steel liquid medicine storage tank through the pipeline filter immediately after boiling for 1.5 hours (starting from boiling) to evenly mix the liquid medicine with the liquid medicine obtained from the first decoction;

(3) concentration: pumping the traditional Chinese medicine liquid prepared in step (2) into an inspissator through a pipe to concentrate the same into thick paste, wherein the temperature for the concentration is 80° C., and the relative density of the prepared thick paste is 1.5 at the temperature of 50° C.;

(4) wet granulation (4.1) dry mixing: putting dextrin, maltodextrin, soluble starch and aspartame into an efficient mixer-granulator for mixing and stirring for 15 minutes to obtain a mixture adjuvant;

(4.2) primary sieving: adding batchwise the thick paste extracted from step (3) to the mixture adjuvant for mixing, stirring and granulation at the cutting speed I and the stirring speed I to obtain a soft material which is then subjected to primary sieving using a 12-mesh sieve;

(4.3) drying: putting the sieved particles prepared from step (4.2) into a boiling dryer for drying, wherein the temperature of the materials is controlled to be 80° C., and the moisture of the final materials is controlled to be 3%;

(4.4) secondary sieving: carrying out secondary sieving by using a wig-wag machine, using a 10-mesh sieve; and (4.5) particle selecting: selecting the particles of 10-60 meshes; and (5) packaging: bagging the particles, which have been mixed and have been tested to be qualified, by an automatic packaging machine according to standard operation procedures, wherein the appearance and the loading amount of the bag are timely detected, and corresponding measures are taken if there occurs any abnormality, the bagged particles are sealed and stored in a clean container, with the product name, the lot number, the number, the date and the like indicated for later use; the reference loading amount is 8 g per bag, and the loading limit is 8 g/bag±5%.

Embodiment 3

The solid beverage for conditioning yin deficiency constitution comprises the following components in parts by weight: 34 parts of smoked plum, 35 parts of lilium brownii, 33 parts of polygonatum odoratum, 36 parts of mulberry leaves, 30 parts of mulberries, 31 parts of fresh reed rhizome, 75 parts of oysters, 5 parts of amomum villosum, 33 parts of dextrin, 20 parts of maltodextrin, 48 parts of soluble starch and 0.2 parts of aspartame.

The production method thereof is as follows:

(1) preparation of raw materials: subjecting smoked plum, lilium brownii, polygonatum odoratum, mulberry leaves, mulberry fruits, oysters, fresh reed rhizome and amomum villosum to impurity removal, cleansing, cutting and pulverization, and then mixing them for later use;

(2) decoction: decocting the mixture resulting from step (1) with water twice to obtain a traditional Chinese medicine liquid, wherein the two-time decoction process is carried out as follows:

the first decoction: adding water that is 10 times the weight of the mixture prepared in step (1), heating and boiling the resultant mixture, and pumping the liquid medicine into a stainless-steel liquid medicine storage tank through a pipeline filter immediately after boiling for 1.5 hours (starting from boiling); and the second decoction: adding water that is 8 times the weight of the mixture prepared in step (1), heating and boiling the resultant mixture, and pumping the liquid medicine into the stainless-steel liquid medicine storage tank through the pipeline filter immediately after boiling for 1.5 hours (starting from boiling) to evenly mix the liquid medicine with the liquid medicine obtained from the first decoction;

(3) concentration: pumping the traditional Chinese medicine liquid prepared in step (2) into an inspissator through a pipe to concentrate the same into thick paste, wherein the temperature for the concentration is 75° C., and the relative density of the prepared thick paste is 1.45 at the temperature of 50° C.;

(4) wet granulation (4.1) dry mixing: putting dextrin, maltodextrin, soluble starch and aspartame into an efficient mixer-granulator for mixing and stirring for 15 minutes to obtain a mixture adjuvant;

(4.2) primary sieving: adding batchwise the thick paste extracted from step (3) to the mixture adjuvant for mixing, stirring and granulation at the cutting speed I and the stirring speed I to obtain a soft material which is then subjected to primary sieving using a 12-mesh sieve;

(4.3) drying: putting the sieved particles prepared from step (4.2) into a boiling dryer for drying, wherein the temperature of the materials is controlled to be 78° C., and the moisture of the final materials is controlled to be 3.4%;

(4.4) secondary sieving: carrying out secondary sieving by using a wig-wag machine, using a 10-mesh sieve; and (4.5) particle selecting: selecting the particles of 10-60 meshes; and (5) packaging: bagging the particles, which have been mixed and have been tested to be qualified, by an automatic packaging machine according to standard operation procedures, wherein the appearance and the loading amount of the bag are timely detected, and corresponding measures are taken if there occurs any abnormity, the bagged particles are sealed and stored in a clean container, with the product name, the lot number, the number, the date and the like indicated for later use; the reference loading amount is 8 g per bag, and the loading limit is 8 g/bag±5%.

Embodiment 4

The solid beverage for conditioning yin deficiency constitution comprises the following components in parts by weight: 47 parts of smoked plum, 45 parts of lilium brownii, 47 parts of polygonatum odoratum, 48 parts of mulberry leaves, 43 parts of mulberries, 50 parts of fresh reed rhizome, 87 parts of oysters, 11 parts of amomum villosum, 44 parts of dextrin, 35 parts of maltodextrin, 60 parts of soluble starch and 0.3 parts of aspartame.

The production method thereof is as follows:

(1) preparation of raw materials: subjecting smoked plum, lilium brownii, polygonatum odoratum, mulberry leaves, mulberry fruits, oysters, fresh reed rhizome and amomum villosum to impurity removal, cleansing, cutting and pulverization, and then mixing them for later use;

(2) decoction: decocting the mixture resulting from step (1) with water twice to obtain a traditional Chinese medicine liquid, wherein the two-time decoction process is carried out as follows:

the first decoction: adding water that is 10 times the weight of the mixture prepared in step (1), heating and boiling the resultant mixture, and pumping the liquid medicine into a stainless-steel liquid medicine storage tank through a pipeline filter immediately after boiling for 1.5 hours (starting from boiling); and the second decoction: adding water that is 8 times the weight of the mixture prepared in step (1), heating and boiling the resultant mixture, and pumping the liquid medicine into the stainless-steel liquid medicine storage tank through the pipeline filter immediately after boiling for 1.5 hours (starting from boiling) to evenly mix the liquid medicine with the liquid medicine obtained from the first decoction;

(3) concentration: pumping the traditional Chinese medicine liquid prepared in step (2) into an inspissator through a pipe to concentrate the same into thick paste, wherein the temperature for the concentration is 73° C., and the relative density of the prepared thick paste is 1.33 at the temperature of 50° C.;

(4) wet granulation (4.1) dry mixing: putting dextrin, maltodextrin, soluble starch and aspartame into an efficient mixer-granulator for mixing and stirring for 15 minutes to obtain a mixture adjuvant;

(4.2) primary sieving: adding batchwise the thick paste extracted from step (3) to the mixture adjuvant for mixing, stirring and granulation at the cutting speed I and the stirring speed I to obtain a soft material which is then subjected to primary sieving using a 12-mesh sieve;

(4.3) drying: putting the sieved particles prepared from step (4.2) into a boiling dryer for drying, wherein the temperature of the materials is controlled to be 72° C., and the moisture of the final materials is controlled to be 4.5%;

(4.4) secondary sieving: carrying out secondary sieving by using a wig-wag machine, using a 10-mesh sieve; and (4.5) particle selecting: selecting the particles of 10-60 meshes; and (5) packaging: bagging the particles, which have been mixed and have been tested to be qualified, by an automatic packaging machine according to standard operation procedures, wherein the appearance and the loading amount of the bag are timely detected, and corresponding measures are taken if there occurs any abnormity, the bagged particles are sealed and stored in a clean container, with the product name, the lot number, the number, the date and the like indicated for later use; the reference loading amount is 8 g per bag, and the loading limit is 8 g/bag±5%.

Embodiment 5

The solid beverage for conditioning yin deficiency constitution comprises the following components in parts by weight: 40 parts of smoked plum, 40 parts of lilium brownii, 40 parts of polygonatum odoratum, 40 parts of mulberry leaves, 40 parts of mulberries, 40 parts of fresh reed rhizome, 80 parts of oysters, 8 parts of amomum villosum, 37 parts of dextrin, 31 parts of maltodextrin, 56 parts of soluble starch and 0.25 parts of aspartame.

The production method thereof is as follows:

(1) preparation of raw materials: subjecting smoked plum, lilium brownii, polygonatum odoratum, mulberry leaves, mulberry fruits, oysters, fresh reed rhizome and amomum villosum to impurity removal, cleansing, cutting and pulverization, and then mixing them for later use;

(2) decoction: decocting the mixture resulting from step (1) with water twice to obtain a traditional Chinese medicine liquid, wherein the two-time decoction process is carried out as follows:

the first decoction: adding water that is 10 times the weight of the mixture prepared in step (1), heating and boiling the resultant mixture, and pumping the liquid medicine into a stainless-steel liquid medicine storage tank through a pipeline filter immediately after boiling for 1.5 hours (starting from boiling); and the second decoction: adding water that is 8 times the weight of the mixture prepared in step (1), heating and boiling the resultant mixture, and pumping the liquid medicine into the stainless-steel liquid medicine storage tank through the pipeline filter immediately after boiling for 1.5 hours (starting from boiling) to evenly mix the liquid medicine with the liquid medicine obtained from the first decoction;

(3) concentration: pumping the traditional Chinese medicine liquid prepared in step (2) into an inspissator through a pipe to concentrate the same into thick paste, wherein the temperature for the concentration is 77° C., and the relative density of the prepared thick paste is 1.4 at the temperature of 50° C.;

(4) wet granulation (4.1) dry mixing: putting dextrin, maltodextrin, soluble starch and aspartame into an efficient mixer-granulator for mixing and stirring for 15 minutes to obtain a mixture adjuvant;

(4.2) primary sieving: adding batchwise the thick paste extracted from step (3) to the mixture adjuvant for mixing, stirring and granulation at the cutting speed I and the stirring speed I to obtain a soft material which is then subjected to primary sieving using a 12-mesh sieve;

(4.3) drying: putting the sieved particles prepared from step (4.2) into a boiling dryer for drying, wherein the temperature of the materials is controlled to be 76° C., and the moisture of the final materials is controlled to be 3.8%;

(4.4) secondary sieving: carrying out secondary sieving by using a wig-wag machine, using a 10-mesh sieve; and (4.5) particle selecting: selecting the particles of 10-60 meshes; and (5) packaging: bagging the particles, which have been mixed and have been tested to be qualified, by an automatic packaging machine according to standard operation procedures, wherein the appearance and the loading amount of the bag are timely detected, and corresponding measures are taken if there occurs any abnormity, the bagged particles are sealed and stored in a clean container, with the product name, the lot number, the number, the date and the like indicated for later use; the reference loading amount is 8 g per bag, and the loading limit is 8 g/bag±5%.

Experimental Example 1: The Following is a Test for the Effects of the Solid Beverage for Conditioning Yin Deficiency Constitution, which is Prepared According to Embodiment 5 of the Present Invention The basic conditions of the cases: 150 clinical cases of yin deficiency constitution, including 80 male cases and 70 female cases. 20 cases suffered from dry cough, had reduced sputum which was also sticky and white, or had blood-tinged sputum, laryngoxerosis, red tongue with scant liquid, and thready rapid pulse; 20 cases suffered from insomnia and dreamful sleep, dysphoria in chestpalms-soles, palpitation, red tongue with scant liquid, and thready rapid pulse; 20 cases suffered from anorexia, hard bound stool, mouth and lip dryness, or even retching, red tongue with scant liquid, and thready rapid pulse; 20 cases suffered from dryness in the eyes, headache and vertigo, dim eyesight, red tongue with scant liquid, and thready rapid pulse; 20 cases suffered from lumbago and weakness of the legs, dizziness and tinnitus, spermatorrhea and amnesia, oliguria, hair and skin dryness, red tongue with scant liquid, with little or even no coating, and thready rapid pulse; 50 cases had other symptoms of yin deficiency constitution.

The usage and dosage: the solid beverage was administered 8 g each time, twice a day; and was administered after being brewed with boiling water.

The evaluation criteria for therapeutic effects:

Being cured: the clinical symptoms were completely eliminated, and normal life was restored.

Being effective: the clinical symptoms were partially eliminated, and various signs were gradually improved.

Being ineffective: the symptoms and signs were not obviously improved.

Result statistics: 85 cases were cured, the solid beverage was effective to 47 cases and ineffective to 18 cases, i.e., the solid beverage was effective to 132 cases in total, therefore the total effective rate was 88%.

Experimental Example 2: Sensory Evaluation

The solid beverages prepared in embodiments 1-5 were brewed with boiling water and used as experimental groups, and the mixed liquid medicine after two decoctions prepared in the process step (2) in embodiment 5 was used a control group, three replicates of samples were collected from each of the experimental groups and the control group, and were subjected to sensory evaluation by 20 professional sensory assessors. The sensory evaluation scoring criteria are shown in table 1, and the sensory evaluation results are shown in table 2.

TABLE 1

Sensory Evaluation Scoring Criteria

| items | sensory evaluation | score |
|---|---|---|
| color | relatively dark | 1 |
|  | intermediate | 5 |
|  | relatively light | 1 |
| smell | strong smell of traditional Chinese medicine | 1 |
|  | light smell of traditional Chinese medicine | 3 |
|  | medicine fragrance | 5 |
|  | relatively light | 3 |
|  | light | 1 |
| taste | bitter and astringent | 1 |
|  | relatively bitter | 3 |
|  | fragrant and sweet | 5 |
|  | relatively sweet | 3 |
|  | excessively sweet | 1 |
| fineness and smoothness | fine and smooth | 5 |
|  | having granular sensation | 3 |
|  | having a throat-scratching feeling | 1 |
|  | being hard to swallow | 0 |
| overall evaluation | poor | — |
|  | ordinary | — |
|  | good | — |

TABLE 2

Sensory Evaluation Results of Solid Beverages

| | | control group | experimental groups | | | | | |
|---|---|---|---|---|---|---|---|---|
| | items | | embodiment 1 | embodiment 2 | embodiment 3 | embodiment 4 | embodiment 5 | average |
| sensory evaluation (marks) | color | 33 | 95 | 97 | 92 | 90 | 95 | 93.8 |
| | smell | 52 | 92 | 95 | 95 | 94 | 90 | 93.2 |
| | taste | 46 | 96 | 91 | 90 | 93 | 91 | 92.2 |
| | fineness and smoothness | 58 | 90 | 93 | 94 | 94 | 93 | 92.8 |
| | average | 47.25 | 93.25 | 94 | 92.75 | 92.75 | 92.25 | |
| overall evaluation (person-time) | good | 5 | 19 | 18 | 20 | 19 | 20 | 19.2 |
| | ordinary | 7 | 1 | 2 | 0 | 1 | 0 | 0.8 |
| | poor | 8 | 0 | 0 | 0 | 0 | 0 | 0 |

As can be known from the above experimental results, the average scores on the aspects of color, smell, taste and fineness and smoothness of the solid beverages prepared in embodiments 1 to 5 as given by the 20 professional sensory assessors are all higher than the corresponding scores given for the control group. The results show that the solid beverage provided by the present invention is greatly improved in smell and taste, as compared with the liquid medicine obtained by decocting the traditional Chinese medicine decoction pieces, moreover, sweet flavor has been added thereto, the taste and the fine and smooth feeling are greatly improved, which makes the solid beverage provided by the present invention very suitable for everyday drinking.

Experimental Example 3: The Experimental Study on the Product of the Present Invention in Assisting the Mice in Improving Yin Deficiency Syndrome (1) Experimental Principle:

Pathological models of mice suffering from yin deficiency were prepared with thyroxine in combination with reserpine, and the effects of the drugs for improving the yin deficiency of the mice were evaluated through an anti-fatigue test.

(2) Experimental Materials:

The solid beverage particles prepared in embodiments 1-5.

Experimental animals: ICR mice, 200±20 g.

(3) Test Method:

90 ICR mice were divided into nine groups randomly, which were a normal control group, a yin-deficiency model group, experimental groups of embodiments 1-5 (dosage: 0.3 g/kg), and the drugs were intragastrically administered to each group for four weeks. After 20 days of intragastric administration, all the groups, except the normal control group, were intragastrically administered with thyroxine (3 mg per mouse) plus reserpine (0.02 mg per mouse), once a day for 10 times continuously. Half an hour after the last administration, the tail of each of the mice was loaded with solder wires having a weight of 10% of the body weight of the mouse, then the mice were put into room temperature (25° C.) water, and the survival time of the mice was measured.

(4) Statistical Method

The calculated data were expressed by average±standard deviations, and t test was used for intergroup difference comparison, and the results were obtained by using EXCEL statistical software. $p<0.05$ means that there is a significant difference, and $p<0.01$ means that there is a highly significant difference.

(5) The Experimental Results are Shown in Table 3.

TABLE 3

Impact of the Product on Loaded Swimming Time of Mice

| groups | loaded swimming time (s) |
|---|---|
| normal control group | 146 ± 16.3 |
| yin-deficiency model group | 80 ± 11.8 |
| embodiment 1 | 142 ± 14.3* |
| embodiment 2 | 148 ± 15.7* |
| embodiment 3 | 137 ± 13.9* |
| embodiment 4 | 140 ± 12.6* |
| embodiment 5 | 147 ± 13.4* |

Compared with the model group, *$p<0.05$, which means that there is a significance difference.

The experimental data show: the solid beverage particles corresponding to embodiments 1-5 can improve the loaded swimming time of the mice, and have the effect of improving the physical fatigue of the yin-deficiency model mice.

The descriptions above are only preferred embodiments of the present invention, which are not used to limit the present invention. For a person skilled in the art, the present invention may have various changes and variations. Any modifications, equivalent substitutions, improvements etc. within the spirit and principle of the present invention shall all be included in the scope of protection of the present invention.

What is claimed is:

1. A solid beverage mix, characterized by comprising the following components in parts by weight: 30-55 parts of smoked plum, 29-51 parts of *lilium brownii*, 27-50 parts of *polygonatum odoratum*, 30-52 parts of mulberry leaves, 27-48 parts of mulberries, 26-58 parts of fresh reed rhizome, 67-94 parts of oysters, 3-15 parts of amomum *villosum*, 27-50 parts of dextrin, 16-43 parts of maltodextrin, 38-70 parts of soluble starch and 0.15-0.35 parts of aspartame.

2. The solid beverage mix according to claim 1, characterized by comprising the following components in parts by weight: 34-47 parts of smoked plum, 35-45 parts of *lilium brownii*, 33-47 parts of *polygonatum odoratum*, 36-48 parts of mulberry leaves, 30-43 parts of mulberries, 31-50 parts of fresh reed rhizome, 75-87 parts of oysters, 5-11 parts of amomum *villosum*, 33-44 parts of dextrin, 20-35 parts of maltodextrin, 48-60 parts of soluble starch and 0.2-0.3 parts of aspartame.

3. The solid beverage mix according to claim 1, characterized by comprising the following components in parts by weight: 40 parts of smoked plum, 40 parts of *lilium brownii*, 40 parts of *polygonatum odoratum*, 40 parts of mulberry leaves, 40 parts of mulberries, 40 parts of fresh reed rhizome, 80 parts of oysters, 8 parts of amomum *villosum*, 37 parts of dextrin, 31 parts of maltodextrin, 56 parts of soluble starch and 0.25 parts of aspartame.

4. A method for producing a solid beverage mix, characterized by comprising the steps of:

(1) preparation of raw materials: subjecting smoked plum, *lilium brownii, polygonatum odoratum*, mulberry leaves, mulberry fruits, oysters, fresh reed rhizome and amomum *villosum* to cleansing, cutting and pulverization, and then mixing them for later use;

(2) decoction: decocting the mixture resulting from step (1) with water twice to obtain a miscible liquid;

(3) concentration: pumping the miscible liquid prepared in step (2) into an inspissator through a pipe to concentrate the same into thick paste; and (4) wet granulation: mixing and stirring dextrin, maltodextrin, soluble starch and aspartame to obtain a mixture adjuvant, adding the thick paste prepared in step (3) to the mixture adjuvant, and stirring the same for granulation.

5. The method according to claim 4, characterized in that, the two-time decoction process in step (2) is carried out as follows:

the first decoction: adding water that is 10 times the weight of the mixture prepared in step (1), heating and boiling the resultant mixture, and pumping the liquid medicine into a stainless-steel liquid medicine storage tank through a pipeline filter immediately after boiling for 1.5 hours (starting from boiling); and the second decoction: adding water that is 8 times the weight of the mixture prepared in step (1), heating and boiling the resultant mixture, and pumping the liquid medicine into the stainless-steel liquid medicine storage tank through the pipeline filter immediately after boiling for 1.5 hours (starting from boiling) to evenly mix the liquid medicine with the liquid medicine obtained from the first decoction.

6. The method according to claim 4, characterized in that, the temperature for the concentration in step (3) is 70-80° C., and the relative density of the prepared thick paste is 1.2-1.5 at the temperature of 50° C.

7. The method according to claim 4, characterized in that, the wet granulation in step (4) comprises the steps of:
(4.1) dry mixing: putting dextrin, maltodextrin, soluble starch and aspartame into mixer-granulator for mixing and stirring for 15 minutes to obtain a mixture adjuvant;
(4.2) primary sieving: adding batchwise the thick paste extracted from step (3) to the mixture adjuvant for mixing, stirring and granulation at cutting speed I and stirring speed I to obtain a soft material which is then subjected to primary sieving;
(4.3) drying: putting the sieved particles prepared from step (4.2) into a boiling dryer for drying; and
(4.4) secondary sieving: carrying out secondary sieving by using a oscillating granulator.

8. The method according to claim 7, characterized in that, the sieve for the primary sieving is a 12-mesh sieve, and the sieve for the secondary sieving is a 10-mesh sieve.

9. The method according to claim 7, characterized in that, in the drying process in step (4.3), the temperature of the materials is controlled to be 70-80° C., and the moisture of the final materials is controlled to be 5% or less.

10. The method according to claim 7, characterized in that, after the secondary sieving, the method further comprises a particle selecting step to select particles of 10-60 meshes.

* * * * *